US010426765B2

(12) United States Patent
Waetzig et al.

(10) Patent No.: US 10,426,765 B2
(45) Date of Patent: Oct. 1, 2019

(54) PHARMACEUTICAL COMPOSITION CONTAINING NICOTINIC ACID AND/OR NICOTINAMIDE AND/OR TRYPTOPHAN FOR POSITIVELY INFLUENCING THE INTESTINAL MICROBIOTA (71) Applicant: CONARIS RESEARCH INSTITUTE AG, Kiel (DE)

(72) Inventors: Georg Waetzig, Kiel (DE); Dirk Seegert, Dänischenhagen (DE)

(73) Assignee: CONARIS RESEARCH INSTITUTE AG, Kiel (DE)

( * ) Notice: Subject to any disclaimer, the term of this patent is extended or adjusted under 35 U.S.C. 154(b) by 3 days.

(21) Appl. No.: 14/407,780

(22) PCT Filed: Jun. 14, 2013

(86) PCT No.: PCT/EP2013/062363
§ 371 (c)(1),
(2) Date: Dec. 12, 2014

(87) PCT Pub. No.: WO2013/186355
PCT Pub. Date: Dec. 19, 2013

(65) Prior Publication Data
US 2015/0126462 A1 May 7, 2015

(30) Foreign Application Priority Data

Jun. 15, 2012 (DE) .................. 10 2012 011 890

(51) Int. Cl.
| *A61K 31/455* | (2006.01) |
| *A61K 9/00* | (2006.01) |
| *A61K 31/405* | (2006.01) |
| *A61K 9/28* | (2006.01) |
| *A61K 9/50* | (2006.01) |
| *A61K 38/05* | (2006.01) |
| *A61K 45/06* | (2006.01) |

(52) U.S. Cl.
CPC .......... *A61K 31/455* (2013.01); *A61K 9/0031* (2013.01); *A61K 9/284* (2013.01); *A61K 9/5047* (2013.01); *A61K 31/405* (2013.01); *A61K 38/05* (2013.01); *A61K 45/06* (2013.01)

(58) Field of Classification Search
None
See application file for complete search history.

(56) References Cited

U.S. PATENT DOCUMENTS

| 6,129,930 | A | 10/2000 | Bova |
| 6,713,057 | B1 | 3/2004 | Chatterjee |
| 2005/0063902 | A1 | 3/2005 | Zeligs |
| 2005/0159396 | A1 | 7/2005 | Harty |
| 2006/0264409 | A1 | 11/2006 | Harty |
| 2008/0108684 | A1 | 5/2008 | Matsumoto et al. |
| 2008/0113031 | A1* | 5/2008 | Moodley ............... A61K 9/5073 424/490 |
| 2009/0104171 | A1* | 4/2009 | Pardee .................. A61K 31/198 424/94.1 |
| 2010/0086588 | A1 | 4/2010 | Forbes |
| 2015/0126462 | A1 | 5/2015 | Waetzig et al. |
| 2016/0136147 | A1 | 5/2016 | Højgaard et al. |

FOREIGN PATENT DOCUMENTS

| JP | 2011-121889 A | 6/2011 |
| JP | 2012-102054 A | 5/2012 |
| WO | WO 97/2880 * | 8/1997 |
| WO | WO 97/28801 A1 | 8/1997 |
| WO | WO 97/29760 * | 8/1997 |
| WO | WO 97/29760 A1 | 8/1997 |
| WO | WO 98/02148 A2 | 1/1998 |
| WO | WO 02/11725 A1 | 2/2002 |
| WO | WO-2004/066910 A2 | 8/2004 |
| WO | WO 2005/115075 A2 | 12/2005 |
| WO | WO 2008/044099 A1 | 4/2008 |
| WO | WO 2009/131537 * | 10/2009 |
| WO | WO 2009/131537 A1 | 10/2009 |
| WO | WO 2009/149058 A2 | 12/2009 |
| WO | WO 2012/090224 A1 | 7/2012 |
| WO | WO-2017/184563 A1 | 10/2017 |

OTHER PUBLICATIONS

Hashimoto Jul. 26, 2012 | vol. 487 | Nature | 477-481.*
Website: http://www.newmediaexplorer.org/sepp/2012/01/25/does_smoking_tobacco_fulfill_a_nutritional_need.htm, Retrieved on Oct. 27, 2016.*
Benowitz et al., "Nicotine Chemistry, Metabolism, Kinetics and Biomarkers," Handbook Exp. Pharmacol., 192: 29-60 (2009).*
The SIDS Initial Assessment Report, 2002, 1-19.*
Sanyal, 2010, Drugs of Today, 46(6), 371-378.*
'European Food Safety Authority' 2006, pp. 121-133.*
Nainggolan on website: http://www.medscape.com/viewarticle/777519_print, 2pages, retreived on Apr. 9, 2017.*
Website: https://www.drugs.com/drug-class/prostaglandin-d2-antagonists.html, 1 page, retreived on Apr. 9, 2017.*
Abdu-Allah, Bulletin of Pharmaceutical Sciences, Assiut University, vol. 28, No. 2, pp. 237-253 (2005).*
Kim, Journal of Nutritional Biochemistry 21 (2010) 468-475.*
International Search Report dated Jul. 16, 2013 in application No. PCT/EP2013/062363.
European Search Report dated Feb. 19, 2014 in application No. EP 13197261.
Bettenworth et al., "Nicotinamide Ameliorates the Course of Citrobacter Rodentium-Induced Colitis Through Enhanced Bacterial Killing," Gastroenterology, vol. 142, No. 5, p. S685, May 2012.
Lu et al., "Pellagra in an Immunocompetent Patient with Cytomegalovirus Colitis," Am. J. Gastroenterol., vol. 96, pp. 932-934, 2001.

(Continued)

Primary Examiner — Satyanarayana R Gudibande
(74) Attorney, Agent, or Firm — Foley & Lardner LLP (57) ABSTRACT

The present invention relates to a new pharmaceutical composition containing nicotinic acid, nicotinamide, tryptophanor related compounds for positively influencing the intestinal microbiota. In certain embodiments, the pharmaceutical composition is partially or entirely released into the small intestine or large intestine.

24 Claims, 7 Drawing Sheets

(56) References Cited

OTHER PUBLICATIONS

Penberthy, "Pharmacological Targeting of IDO-Mediated Tolerance for Treating Autoimmune Disease," Curr. Drug Metab., vol. 8, pp. 245-266, 2007.
Sanchez-Fidalgo, "PARP inhibition reduces acute chronic inflammation in rats," Eur. J. Pharmacol., vol. 563, pp. 216-223, 2007.
Filippi et al., "Nutritional Deficiencies in Patients with Crohn's Disease in Remission," Inflamm. Bowel Disease, vol. 12, pp. 185-191, 2006.
Glenn et al., "Synthesis and Mass Spectrometry of Some Structurally Related Nicotinoids," J. Org. Chem., vol. 43, No. 14, pp. 2860-2870, 1978.
Dominiak et al., "Effects of Nicotine and its Major Metabolites on Blood Pressure in Anaesthetized Rats," Klin. Wochenschr., vol. 63, pp. 90-92, 1985.
Clayton et al., "Pellagra with colitis due to a defect in tryptophan metabolism," Eur. J. Pediatr., vol. 150, pp. 498-502, 1991.
Osman et al., "Bifidobacterium infantis strains with and without a combination of Oligofructose and Inulin (OFI) attenuate inflammation in DSS-induced colitis in rats," BMC Gastroenterology, vol. 6, No. 31, doi: 10.1186/1471-230X/6/31, Oct. 28, 2006.
Mazmanian et al., "A microbial symbiosis factor prevents intestinal inflammatory disease," Nature, vol. 453, pp. 620-625, May 29, 2008.
Segal et al., "Rectal manifestations of pellagra," Intl. Journal of Colorectal Disease, vol. 1, pp. 238-243, 1986.
Frank et al., "Molecular-phylogenetic characterization of microbial community imbalances in human inflammatory bowel diseases," PNAS, vol. 103, No. 34, pp. 13780-13785, Aug. 21, 2007.
Kim et al., "L-Tryptophan exhibits therapeutic function in a porcine model of dextran sodium sulfate (DSS)-induced colitis," Journ. of Nutritional Biochemistry, vol. 21, pp. 468-475 (2010).
Functions of Vitamin B3, Common Knowledge of Nutrition 1-17 Jan. 1, 2000 http://www.dharmazen.org/X1Chinese/D32Health/H208VitB3.htm [Sections 1 and 6].
Abdu-Allah, et al., "Synthesis of Trigonelline and Nicotinamide Linked Prodrugs of 5-aminosallcylic acid (5-ASA) with Analgesic and Anti-Inflammatory Effects," Bulletin of Pharmaceutical Sciences, Assiut University, vol. 28, No. 2, pp. 237-253 (2005).
Non-Final Office Action issued in co-pending U.S. Appl. No. 15/103,410, dated Aug. 30, 2017 (US 2017/0027924).
PCT/US2017/028063, Apr. 18, 2017, Ferring B V.
Office Action dated Mar. 22, 2018 in U.S. Appl. No. 15/103,410 (US 2017-0027924).
Office Action dated Jan. 30, 2018 in U.S. Appl. No. 15/103,406 (US 2016-0317557).
Office Action dated Feb. 12, 2018 in U.S. Appl. No. 15/103,406 (US 2016-0317557).
Betterworth, "Nicotinamide Ameliorates the Course of Citrobacter Rodentium-Inducted Colitis Through Enhanced Bacterial Killing," Gastroenterology, vol. 142, No. 5, p. S658 (May 2012).
Andrews et al., "Mesalazine (5-aminosalicylic acid) Alters Faecal Bacterial Profiles, but not Mucosal Proteolytic Activity in Diarrhea-Predominant Irritable Bowel Syndrome," AP&T Alimentary Pharmacology and Therapeutics (2011) vol. 34, pp. 374-383.
Caesar et al., "Effects of gut microbiota on obesity and atherosclerosis via modulation of inflammation and lipid metabolism," Journal of Internal Medicine, vol. 268, No. 4, pp. 320-328.
Elam et al., "Effect of Niacin on Lipid and Lipoprotein Levels and Glycemic Control in Patients with Diabetes and Peripheral Arterial Disease," JAMA, vol. 284, No. 10, pp. 1263-1270, Sep. 2000.
Final Office Action issued in co-pending U.S. Appl. No. 15/103,406, dated Aug. 31, 2017 (US 2016/0317557).
Gopal et al., "Transport of Nicotinate and Structurally Related Compounds by Human SMCT1 (SLC5A8) and Its Relevance to Drug Transport in the Mammalian Intestinal Tract," Pharmaceutical Research, (Mar. 2007) vol. 24, No. 3, pp. 575-584.
International Search Report dated Jun. 19, 2015 in application No. PCT/EP2014/077646.
Koren et al., "Human oral, gut, and plaque microbiota in patients with atherosclerosis," PNAS, vol. 108, Suppl. 1, pp. 4592-4598, Mar. 2011.
Lawrance, "Topical Agents for Idiopathic Distal Colitis and Proctitis," Journal of Gastroenterology and Hepatology (2011) vol. 26., pp. 36-43.
Marriott et al., "Pharmaceutical Compounding and Dispensing" (2005)pp. 1-305.
McKenney et al., "Effect of Niacin and Atorvastatin on Lipoprotein Subclasses in Patients with Atherogenic Dyslipidemia," Am. J. Cardiol., vol. 88, pp. 270-274, Aug. 2001.
Norwich Pharmaceuticals, Inc., "NIASPAN," Prescribing information, Mar. 2013, retrieved from the Internet: http://www.rxabbvie.com/pdf/niaspan.pdf.
Notice of Reasons for Rejection dated Mar. 27, 2018 in Japanese Application No. 2015-516627.
Ott et al., "Detection of Diverse Bacterial Signatures in Atherosclerotic Lesions of Patients with Coronary Heart Disease," Circulation, vol. 113, pp. 929-937, Feb. 2006.
Seed et al., "The effect of nicotinic acid and acipimox on liporprotein(a) concentration and turnover," Atherosclerosis, vol. 101, pp. 61-68, 1993.
Tiwari et al., "Drug Delivery Systems: An Updated Review," Int. J. Pharm Investig. (2012) vol. 2, No. 1, pp. 2-11.
Vrieze et al., "The environment within: how gut microbiota may influence metabolism and body composition," Dibetologia, vol. 53, pp. 606-613, Jan. 2010.
Wahlberg et al., "Effects of nicotinic acid on serum cholesterol concentrations of high density lipoprotein subfractions HDL2 and HDL3 in hyperlipoproteinaemia," Journal of Internal Medicine, vol. 228, pp. 151-157, 1990.
Bays et al., "Safety of Niacin and Simvastatin Combination Therapy," The American Journal of Cardiology, vol. 101, Issue 8, Supplement, pp. S3-S8 (2008).
Cheng et al., "Antagonism of the prostaglandin D2 receptor 1 suppresses nicotinic acid-induced vasodilation in mice and humans," PNAS, vol. 103, No. 17, pp. 6682-6687 (Apr. 2006).
Damman et al., "Salicylates and the Microbiota: A New Mechanistic Understanding of an Ancient Drug's Role in Dermatological and Gastrointestinal Disease," Drug Development Research, vol. 74, pp. 344-352 (2013).
Fangmann et al., "Targeted Microbiome Intervention by Microencapsulated Delayed-Release Niacin Beneficially Affects Insulin Sensitivity in Humans," Diabetes Care, vol. 41, pp. 398-405 (Mar. 2018).
Lai et al., "Suppression of Niacin-induced Vasodilation with an Antagonist to Prostaglandin d2 Receptor Subtype 1," Clinical Pharmacology & Therapeutics, vol. 81. No. 6, pp. 849-857 (Jun. 2007).
Myvmc, "Gastrointestinal system anatomy," available on the internet <URL: https://www.myvmc.com/anatomy/gastrointestinal-system/> (2006).
Oberwittler et al., "Clinical evidence for use of acetyl salicylic acid in control of flushing related to nicotinic acid treatment," The International Journal of Clinical Practice, vol. 60, Issue 6, pp. 707-715 (Jun. 2006).
Office Action dated Aug. 9, 2018 in U.S. Appl. No. 15/103,406 (US 2016-0317557).
Office Action dated Oct. 31, 2018 in U.S. Appl. No. 15/103,410 (US 2017/0027924).
Perrie et al., "Controlling Drug Delivery," FASTtrack Pharmaceutics: Drug Delivery and Targeting, second edition, chapter 1 (2012).
Schacht et al., "Polymers for colon specific drug delivery," Journal of Controlled Release, vol. 36, pp. 327-338 (1996).
Williams et al., "Optimizing clinical use of mesalazine (5-aminosalicylic acid) in inflammatory bowel disease," Therapeutic Advances in Gastroenterology, vol. 4, No. 4, pp. 237-248 (2011).
Wan et al., "Advances in the research of niacin deficiency," J. Pract. Dermatolol., vol. 4, No. 4, pp. 219-222, Dec. 2011.
Office Action dated Sep. 26, 2016 in Chinese application No. 201380031622.4.
Office Action dated May 16, 2019 in U.S. Appl. No. 15/103,410 (U.S. 2017-0027924).

(56) References Cited

OTHER PUBLICATIONS

Office Action dated May 30, 2019 in U.S. Appl. No. 15/103,406 (U.S. 2016-0317557).

* cited by examiner

PHARMACEUTICAL COMPOSITION CONTAINING NICOTINIC ACID AND/OR NICOTINAMIDE AND/OR TRYPTOPHAN FOR POSITIVELY INFLUENCING THE INTESTINAL MICROBIOTA

FIELD OF THE INVENTION

The present invention relates to a new pharmaceutical composition containing nicotinic acid and/or nicotinamide and/or tryptophan for positively influencing the intestinal microbiota, wherein the pharmaceutical composition is specifically released (e.g., selectively released) into the small intestine and/or large intestine.

BACKGROUND

Many inflammatory diseases of the intestinal wall are caused or influenced by changes in the intestinal microbiota and/or an impaired interaction between the intestinal microbiota and the intestines. Such intestinal inflammations occur in humans, e.g., inflammatory bowel diseases (IBD), such as Crohn's disease or ulcerative colitis, but also in other mammals (e.g., chronic idiopathic colitis in dogs). These diseases are based on complex immunological processes which are not fully understood. However, changes in, and impaired interactions of, the intestinal microbiota can also be causative factors in a number of other diseases. Examples include atopic diseases, such as atopic eczema, allergic conditions or asthma (see e.g., Bisgaard et al. 2011, J. Allergy Clin. Immunol. 128:646; Iebba et al. 2011, Dig. Dis. 29:531; Abrahamsson et al. 2012, J. Allergy Clin. Immunol. 129:434; Candela et al. 2012, BMC Microbiol. 12:95; Olszak et al. 2012, Science 336:489), as well as metabolic diseases with an inflammatory component, such as arteriosclerosis with resulting coronary heart diseases, adiposity or diabetes (Ott et al. 2006, Circulation 113:929; Koren et al. 2011, PNAS 108 Suppl 1:4592; for reviews see Caesar et al. 2010, J. Intern. Med. 268:320; and Vrise et al. 2010, Diabetologia 53:606).

Although the relationship between the intestinal microbiota and various diseases is known, it has not been understood how to influence the microbiota in a way that would positively impact associated diseases.

Nicotinic acid (niacin, vitamin B3), nicotinamide (nicotinic acid amide) and/or L-tryptophan have been used for the therapy of niacin deficiency diseases (e.g., pellagra) for decades. It is known that pellagra may be accompanied by intestinal inflammation, which is ameliorated after niacin administration, where the therapeutic principle is the elimination of the vitamin deficiency causing the intestinal inflammation (Segal et al. 1986, Int. J. Colorectal Dis. 1:238; and Clayton et al. 1991, Eur. J. Pediatr. 150:498).

It is also known that nicotinic acid has a health-promoting effect on cholesterol lipoproteins in the blood (HDL/LDL ratio and size of the LDL vesicles; Wahlberg et al. 1990, J. Intern. Med. 228:151; Seed et al. 1993, Atherosclerosis 101:61; Elam et al. 2000, JAMA 284: 1263; McKenney et al. 2001, Am. J. Cardiol. 88:270).

SUMMARY OF THE INVENTION

The object of the present invention is to provide new forms of treatments for the therapy and/or prophylaxis of diseases in humans and animals associated with changes in the intestinal microbiota and/or an impaired interaction between the intestinal microbiota and intestines.

According to the invention, the above problem is solved by a pharmaceutical composition which contains nicotinic acid, nicotinamide, tryptophan or another compound described herein, which is believed to positively influence the intestinal microbiota. In preferred embodiments, the nicotinic acid and/or nicotinamide and/or tryptophan are administered to locally influence the intestinal mucosa and the intestinal microbiota. For example, the active substance is formulated to be administered selectively in the terminal ileum or colon where the intestinal microbiota to be modified are located. Other active substances which convert to nicotinic acid and/or nicotinamide and/or tryptophan in an animal body (e.g., a human body) are also contemplated by the present invention.

Accordingly, pharmaceutical compositions are provided which contain nicotinic acid (niacin, vitamin B3) and/or nicotinamide and/or tryptophan. These three substances act individually or in combination (combination of two or three) with one another in an anti-inflammatory and/or beneficial manner on the microbiota in the small intestine and/or large intestine. The composition is suitable for oral administration with controlled and/or delayed release of the active ingredient for specific local or topical efficacy in the terminal ileum and/or colon. Exemplary conditions treated include therapy or prophylaxis of inflammatory diseases of the small intestine, inflammatory diseases of the large intestine, prophylaxis of colon carcinoma, and therapy or prophylaxis of other diseases which result from changes in the intestinal microbiota and/or an impaired interaction between intestinal microbiota and intestines. The composition is also suitable for the (neo)rectal administration in the colon or pouch for the local and/or topical therapy of inflammatory diseases of the large intestine or pouchitis.

The invention also includes methods of treating one or more of the diseases and conditions described herein with a pharmaceutical composition described herein. In addition, the invention provides the use of a pharmaceutical composition described herein in the manufacture of a medicament for treating one or more of the diseases and conditions described herein.

BRIEF DESCRIPTION OF THE DRAWINGS

FIG. 1 shows prevention of the intensification of DSS colitis in ACE2-deficient mice by nicotinamide or tryptophan. Top row: histopathology of the colon (haematoxylin eosin staining on day 10 after DSS administration; bar: 100 µm (a)), weight loss in percent (b) and diarrhea score (c) of DSS-challenged ACE2-normal (ACE2+/y) and ACE2-deficient (ACE2-/y) mice which were given vehicle or nicotinamide (NAM) in the drinking water. The NAM administration began 3 days before the DSS administration. Bottom row: histopathology of the colon (haematoxylin eosin staining on day 7 after DSS challenge; bar: 100 µm (d)), weight loss in percent (e) and damage of the crypts of the colon (f) in DSS-challenged ACE2-normal (ACE2+/y) and ACE2-deficient (ACE2-/y) mice which received normal diet (control) or a tryptophan-dipeptide diet (Trp+).

All values are average values with standard error of 3-10 mice per group.

*: $P<0.05$; ** or ##: $P<0.01$.

DETAILED DESCRIPTION

The core of the invention is a pharmaceutical composition comprising one, two or more active substance(s) selected from nicotinic acid; nicotinamide; tryptophan; a compound that converts in the body of an animal (e.g., a human body) into nicotinic acid, nicotinamide or tryptophan; nicotinamide adenine dinucleotide (NAD); nicotinamide adenine dinucleotide phosphate (NADP); an intermediate in the biosynthesis of NAD or NADP; and a tryptophan dipeptide, for positively influencing the intestinal microbiota, wherein the pharmaceutical composition is designed for a delayed release so that it releases (e.g., partially releases, selectively releases) in the lower small intestine, the colon or both.

The inventors have recognized that nicotinic acid and/or nicotinamide and/or tryptophan have an anti-inflammatory effect by influencing the intestinal microbiota (the entirety of all microorganisms in the intestines, in particular the bacteria) in that they change the secretion pattern of antimicrobial peptides in the intestines. The altered intestinal microbiota after the administration of a pharmaceutical composition according to the invention have a less inflammation-promoting effect or are anti-inflammatory, thus causing and/or supporting a clear reduction in the symptoms of IBD, such as Crohn's disease or ulcerative colitis, in humans or in other mammals (e.g., chronic idiopathic colitis in dogs). Moreover, it has been demonstrated for the first time herein that pharmaceutical compositions that release at least part of their active substance in the affected area of the gastrointestinal tract have significantly better efficacy than a pharmaceutical composition that is largely absorbed before reaching the affected area.

Thus, as used herein, "positively influencing the intestinal microbiota" refers to causing a change in the intestinal microbiota that has a positive impact on health, especially on one or more of the diseases and conditions described herein. For example, positive impacts are associated with reducing the number of pathogenic bacteria, reducing the ratio of pathogenic bacteria to beneficial bacteria, increasing the diversity of the microbiota, reducing the amount of inflammation that the microbiota induce in the intestines, and partly or completely reverting pathological changes in the enterotype of the microbiota (e.g., enterotypes associated with *Bacteroides, Prevotella* and *Ruminococcus*). Bacteria generally regarded as pathogenic in inflammatory bowel diseases include, for example, Enterobacteriaceae (e.g., *Escherichia coli*) with invasive properties or virulence factors, sulphide-producing *Desulfovibrio* spp. and *Fusobacterium* spp with invasive properties. Bacteria generally regarded as beneficial include species from the genera *Lactobacillus, Bifidobacterium* and *Faecalibacterium*, such as *L. casei, L. plantarum* and *F. prausnitzii*. For a recent overview of the gut microbiota in inflammatory bowel diseases, see Manichanh et al. 2012, Nat. Rev. Gastroenterol. Hepatol. 9:599.

Hashimoto et al. (Nature 2012, 487:477), published after the priority date of this application and the contents of which are incorporated herein by reference, provides additional evidence regarding the invention described herein. Hashimoto et al. showed that malabsorption of tryptophan in mice leads to a significantly increased severity of colitis induced by the irritant dextran sodium sulfate (DSS). Dietary supplementation of tryptophan or nicotinamide prevented this increase in colitis. Hashimoto et al. demonstrated that the increased susceptibility to severe colitis was due to a changed gut microbiome, which when transplanted to other mice also increased colitis severity in the recipients. The detrimental change in the gut microbiome was found to be due to strongly reduced amounts of certain antimicrobial peptides (AMPs), especially alpha-defensins, whose expression in epithelial cells of the terminal ileum were largely controlled by mTOR signalling induced by tryptophan or nicotinamide.

Because chronic intestinal inflammation strongly increases the risk of developing colon carcinoma (for review see e.g., Ullman & Itzkowitz 2011, Gastroenterology 140: 1807), a use of the composition according to the invention is also the prophylaxis of colon carcinoma in the case of a chronic or recurrent intestinal inflammation.

Therapeutic intervention by establishment or re-establishment of a normal gut microbiota or by supplementation of beneficial bacteria has been shown to be efficacious in diverse disease models and in the respective human diseases. For example, Olszak et al. (Science 2012, 336:489) recently demonstrated that the pathological accumulation of invariant natural killer T cells in diseased organs in germ-free murine models of IBD or asthma can be prevented by colonising neonate mice with normal microbiota. In different diseases, studies have demonstrated beneficial effects of certain pre-, pro- or synbiotics. For example, lactobacilli can reduce blood cholesterol levels in obesity, but the mechanism is still not completely clear (reviewed by Caesar et al. 2010, J. Intern. Med. 268:320). In inflammatory bowel diseases, some probiotics like VSL#3 (a mixture of *Bifidobacterium breve, Bifidobacterium longum, Bifidobacterium infantis, Lactobacillus acidophilus, Lactobacillus plantarum, Lactobacillus paracasei, Lactobacillus delbrueckii* ssp. *bulgaricus* and *Streptococcus thermophilus*) have been successfully used in a limited number of clinical studies. It appears that the supplementation of at least several strains of bacteria is usually requisite to provide significant therapeutic benefit. A recent example of spectacular efficacy of a complex bacterial intervention is the successful use of stool transplants against *Clostridium difficile* (van Nood et al. 2013, New Engl. J. Med. 368:407).

Because pathological changes in the intestinal microbiota can also play a causal role in numerous other diseases originating from atopic disorders as well as in metabolic diseases with an inflammatory component, the therapy and/or prophylaxis of such diseases is also within the scope of the invention. In particular, the following diseases are examples for such indications:

skin: allergy, atopic eczema, psoriasis;
lung: cystic fibrosis, asthma, COPD;
vessels: coronary heart disease, arteriosclerosis, atherosclerosis;
endocrine system: diabetes, adiposity.

The inventive, specific, topical use of nicotinic acid and/or nicotinamide and/or tryptophan (and related active substances) for locally influencing the intestinal mucosa and the intestinal microbiota, intestinal inflammations, and the direct therapy of the intestinal mucosa result from the insights described herein into the formerly unknown and unexpected role of these compounds. This use significantly differs from conventional uses of the active substances, where these substances are absorbed and are supposed to act systemically. On account of their new anti-inflammatory effect and/or their effect modifying the intestinal microbiota, nicotinic acid and/or nicotinamide and/or tryptophan (and the other compounds described herein) are thus suitable as active substances for treating inflammatory diseases of the small intestine and/or large intestine. Particular conditions include the treatment of intestinal inflammations, the prophylaxis of colon carcinoma, and the therapy or prophylaxis of other diseases that result from changes in the intestinal microbiota and/or an impaired interaction between the intestinal microbiota and the intestines. Preferably, these active substances are used in a pharmacological formulation that protects the largest possible amount of active substance from being absorbed by the body in the upper small intestine and rather effects a release (e.g., controlled release and/or delayed release) into the terminal ileum or colon where the intestinal microbiota to be modified are located (e.g., the active substance is selectively released in the terminal ileum and/or colon).

In particular, the active substances described herein are thus suitable for being used in medicaments with topical release (e.g., controlled and/or delayed release) for the therapy of Crohn's disease, ulcerative colitis, pouchitis, further chronic diseases of the large intestine or inflammations of the large intestine, diversion colitis, infectious enteritis, antibiotic-associated diarrhea such as *C. difficile*-associated diarrhea, infectious colitis, diverticulitis and inflammations which are formed by irradiation, by antibiotics, by chemotherapeutic agents, by pharmaceutical products or by chemicals, as well as for the prophylaxis of colon carcinoma and for the therapy or prophylaxis of other diseases which result from changes in the intestinal microbiota and/or an impaired interaction between intestinal microbiota and intestines.

The claimed substances are equally usable for the therapy or prophylaxis of diseases with similar genesis in both human and other mammals, in particular in domestic and useful animals. Examples of such animals are dogs, cats, horses, camels or cows without objective restriction.

Active substances, i.e., nicotinic acid and/or nicotinamide and/or tryptophan, may be used in any form available on the market, e.g., produced by Merck KgaA. Tryptophan may be used as a single amino acid or dipeptide, e.g., as a Gly-Trp dipeptide.

In addition to nicotinic acid, nicotinamide and tryptophan, other related compounds can be used in the invention described herein as active substances. For example, compounds that convert into one of these agents (e.g., by hydrolysis, metabolism) in the human or animal body are suitable, such as nicotinic acid esters. In addition, intermediates in the synthesis of nicotinamide adenine dinucleotide (NAD) or NAD phosphate (NADP), such as N-formylkynurenine, L-kynurenine, 3-hydroxy-L-kynurenine, 3-hydroxyanthranilate, 2-amino-3-carboxymuconate semialdehyde, quinolinate, and beta-nicotinate D-ribonucleotide, can be used. Further examples include NAD and NADP.

Pharmaceutical compositions which contain nicotinic acid and/or nicotinamide and/or tryptophan (or one of the other substances described above), can be administered orally with a retarded active substance release or also via a rectal mode of application (e.g., enemas or suppositories). The site of delivery of the active substance is preferably the lower portions of the small intestine and/or the colon for inhibiting inflammatory processes, and thus differs fundamentally from modes of applications which—e.g., for the therapy of pellagra—pursue maximal absorption and metabolism in the organism and thus a systemic effect. In addition, the mode of administration according to the invention and the dosage according to the invention minimise the probability for the occurrence of side effects, for example as described in connection with the systemic administration of nicotinic acid.

As used herein, the "lower small intestine" is the second half of the small intestine and the "terminal ileum" is the second half of the ileum.

In this regard, the present invention also comprises combination preparations, such as combinations of nicotinic acid and/or nicotinamide with acetylsalicylic acid and/or prostaglandin D2 antagonists, such as laropiprant, which reduce the side effects typical of nicotinic acid. The composition and dosage of such combinations is known to a person skilled in the art. In addition, the use of nicotinamide instead of nicotinic acid, which is preferred according to the invention, minimises the probability of the occurrence of side effects.

In order to produce orally administered formulations of an active substance having an anti-inflammatory and/or modifying effect on the intestinal microbiota in the terminal ileum and/or in the colon, it is thus advantageous and innovative to use controlled and/or delayed modes of release. In contrast to conventional (in some cases also delayed) modes of release for optimum supplementation, e.g., in the case of pellagra, certain embodiments of the present invention partially or substantially avoid an absorption in the stomach and in the upper portions of the small intestine.

In order to treat Crohn's disease or ulcerative colitis, oral and/or rectal modes (e.g., as enema) of application are suitable. In order to treat pouchitis in the case of ulcerative colitis, the rectal application (e.g., as enema) is preferred. It can also be supported by an oral administration of the oral formulations described above, e.g., delayed releasing preparations. For the symptomatic therapy of any other form of colitis, both the oral and rectal applications can be chosen for the therapeutic modification of the intestinal microbiota. The oral application is preferred for the prophylaxis of the colon carcinoma, in particular in the case of ulcerative colitis, and for the therapy and/or prophylaxis of other diseases which partially or substantially result from changes in the intestinal microbiota and/or an impaired interaction between intestinal microbiota and the intestines.

For oral administration, particular dosage forms that control and/or delay the release of the active substance due to special galenics (so-called controlled release, slow release or delayed release forms) are particularly suitable. Such dosage forms may be simple tablets and also coated tablets, e.g., film tablets or dragees. The tablets are usually round or biconvex. Oblong tablet forms, which allow the tablet to be separated, are also possible. In addition, granules, spheroids, pellets or microcapsules are possible, which are filled in sachets or capsules, where appropriate.

The term "delayed release" relates preferably to a pharmaceutical formulation that releases the active ingredients after a period of delay. In certain embodiments, the delay is sufficient for at least a portion of the active substances in a formulation to release in the lower small intestine (e.g., terminal ileum) and/or colon.

The term "controlled release" refers preferably to a pharmaceutical formulation or component thereof that releases, or delivers, one or more active ingredients over a prolonged period of time. In certain embodiments, the period of time is sufficient for at least a portion of the active substances in a formulation to release in the lower small intestine (e.g., terminal ileum) and/or colon.

The retardation is advantageously achieved, e.g., by coatings which are resistant to gastric juice and dissolve depending on the pH, by means of microcellulose and/or multi matrix (MMX) technologies, by using different carrier matrices or a combination of these techniques. Examples include film coatings which contain acrylic and/or methacrylate polymers in various mixtures for controlled and/or delayed release. For example, the active substance(s) can be contained in a conventional matrix of microcrystalline cellulose or gelatin or with MMX technology, which is coated with a material, which provides the delayed release of the active substance(s). It is preferred to introduce an active substance in large-volume capsules (e.g., gelatin having a content of 0.68 ml) which are coated by means of known methods. Suitable coating agents are water-insoluble waxes and polymers, such as polymethacrylates (e.g., the product portfolio with the trade name Eudragit®, in particular Eudragit® S and Eudragit® L, Evonik Industries AG, Essen, Germany) and water-insoluble celluloses (e.g., methyl cellulose, ethyl cellulose). Where appropriate, water soluble polymers (e.g., polyvinylpyrrolidone), water-soluble celluloses (e.g., hydroxypropylmethyl cellulose or hydroxypropyl cellulose), polysorbate 80, polyethylene glycol (PEG), lactose or mannitol can also be contained in the coating material.

For example, a combination of Eudragit® S and L compounds (e.g., Eudragit® L/S 100) effects a controlled release of the active substances according to the invention at pH>6.4, which occurs in the terminal ileum. Further uses of Eudragit® preparations and mixtures thereof (L, S and R compounds) are also conceivable for the packaging of an active substance, and therefore a topical use in selected portions of the entire gastrointestinal tract can be achieved by controlled release at certain pH values.

The pharmaceutical composition can also contain further pharmaceutical excipient substances, such as binders, fillers, glidants, lubricants and flow regulating agents. The compounds according to the invention can be formulated, where appropriate, together with further active substances and with excipients conventional in pharmaceutical compositions, e.g., talcum, gum arabic, lactose, starch, magnesium stearate, cocoa butter, aqueous and non-aqueous carriers, lipid components of animal or vegetable origin, paraffin derivatives, glycols (in particular polyethylene glycol), various plasticizers, dispersants, emulsifiers and/or preservatives.

In order to produce enemas or suppositories for rectal application, preparations of an active substance can be dissolved in a suitable solvent and be further processed into enemas or suppositories according to known pharmaceutical methods.

The active substance content in the finished dosage form is 1-3000 mg, preferably 100-1000 mg, in the case of oral administration; the enemas and/or suppositories can contain an amount of 10 mg to 5000 mg of the active substance. Depending on the intensity and severity of the inflammatory disease, the dosage forms are administered once or several times daily or in another dosage regimen to be chosen by a physician.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "prophylaxis" and "prevent" refer to delaying the onset of or reducing the likelihood of developing a disease or disorder or one or more symptoms thereof, as compared to an untreated control population.

A further aspect of the invention described herein is the efficient use of the claimed medicaments on the basis of genetic and/or microbiological data and specific needs of the individuals to be treated. New insights into the genetic predisposition of individuals for all types of diseases (in particular also diseases where the interaction between intestinal microbiota and intestines is impaired) and into pharmacogenetics indicate that an evidence-based personalized medicine including genetic analyses of relevant risk genes and also of genes which code e.g., for cell surface receptors, transporter proteins, metabolism enzymes or signal transduction proteins, which interact with the medicament and/or its metabolites and/or its downstream effectors, can contribute information and improvements with respect to the type of use, the mode of application, the time(s) of use, the dose and/or the dosage regimen of the medicaments described herein. Individuals who may benefit from this personalized treatment include those with reduced serum tryptophan, altered expression of $B^0$ AT1 (e.g., in intestinal epithelial cells) and $B^0$ AT1 polymorphisms. This applies analogously to analyses of the intestinal microbiota, particularly when a stool sample indicates a change in the microbiota. The present invention thus also comprises the use of suitable genetic and/or microbiological test methods to identify individuals particularly susceptible to the medicaments according to the invention and/or to adapt the use of the medicaments according to the invention to the individual circumstances. This also comprises expressly the use of different substances (nicotinic acid and/or nicotinamide and/or tryptophan) in different modes of administration depending on the genetic and microbiological properties of the individual. For these purposes, it is possible to use laboratory tests and/or suitable test kits and also measuring methods, devices and/or kits to be employed by a physician, user and/or patient, e.g., to take stool samples or to analyze suitable parameters in the blood, urine or other body fluids.

EXEMPLIFICATION

There are variable possibilities to advantageously develop, and develop further, the teaching of the present invention. For this purpose, reference is made to the examples below which describe the invention in a representative way.

Example 1

Figure 1:
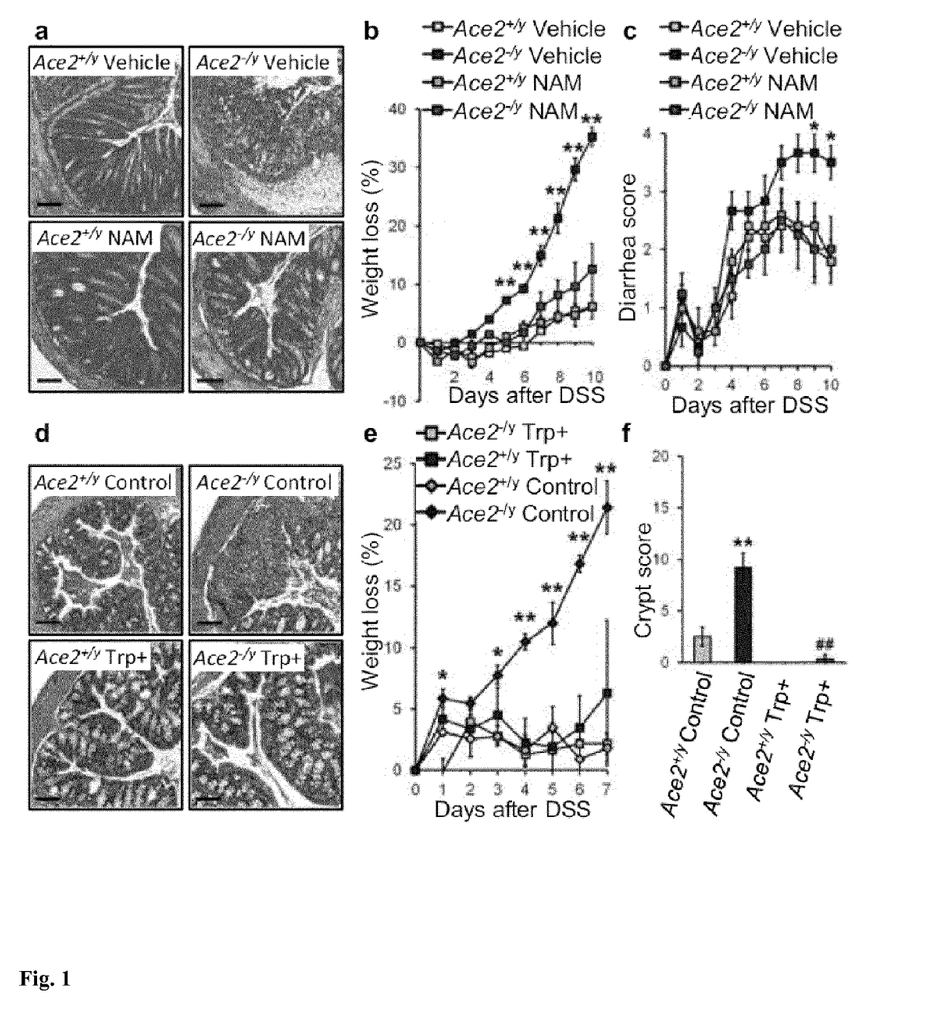

New and findings unpublished at the time the priority application was filed, since published as Hashimoto et al. (Nature 2012, 487:477), support the teachings of the present invention and are briefly described here for the purpose of illustration: It is known that the expression of the transporter for neutral amino acids $B^0$ AT1 (which transports tryptophan) on the surface of intestinal epithelial cells is bound to the presence of the angiotensin converting enzyme 2 (ACE2) (Kowalczuk et al. 2008, FASEB J. 22:2880; Camargo et al. 2009, Gastroenterology 136:872). Defective ACE2 results in an amino acid deficiency disease (so-called Hartnup disease), whose disease pattern is similar to pellagra and which can be treated by an increased supply of tryptophan and nicotinamide. A mouse model has now shown that mice without functioning ACE2 (genotype: Ace2-/y) suffered from substantially stronger artificially induced intestinal inflammations than mice with normal genotype (Ace2+/y) when they were given the substance dextran sodium sulfate (DSS). Interestingly enough, it was possible to reduce this effect by the prophylactic and permanent administration of nicotinamide (NAM) or by fed tryptophan dipeptides (which are taken up via a transporter other than the $B^0$ AT1 which is not available herein) to the value of genetically normal mice. The accompanying data is summarized in FIG. 1 and supports with regard to contents the findings and claims of the present invention for use in man and animal from the perspective of a mouse model.

Example 2

In order to analyze the change in the intestinal microbiota when nicotinamide is given, genomic DNA is isolated from stool samples according to the prior art and quantified, and the variable region of the bacterial 16-S-rRNA gene is amplified, wherein the amplicons are provided with suitable markings for the purpose of identification. Following high throughput pyrosequencing of the amplicons, all sequences obtained are subjected to a quality control and are analyzed by a multi-stage sequence comparison with curated databases of bacterial DNA sequences. Differences of the obtained representative cross-sections of the intestinal microbiota in the stool samples of treated and untreated individuals are correlated and evaluated with the observed and measured disease symptoms and the relevant genetic factors of the individuals.

Figure 2:
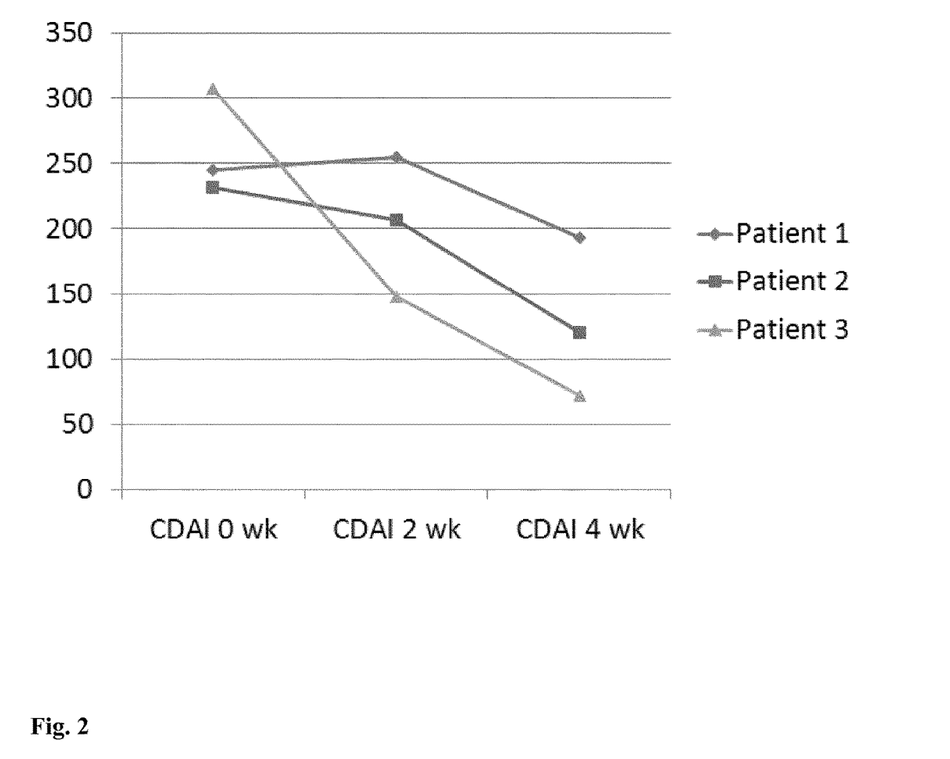
FIG. 2 shows development of the Crohn's disease activity index (CDAI) in three patients from week (wk) 0 to week 4 while administering nicotinamide (2×600 mg daily).

FIG. 2 shows the development of the Crohn's disease activity index (CDAI), i.e., the disease activity calculated according to an acknowledged standard from different disease parameters, of three patients who suffered from Crohn's disease and were treated with conventionally formulated high-dose nicotinamide for 4 weeks (2×600 mg daily). A value of CDAI<150 is equivalent to remission. All three patients suffering from Crohn's disease showed a clear response to the administration of nicotinamide, two of them achieved the remission within the therapy period.

The underlying mechanism and beneficial effect of nicotinamide described by Hashimoto et al. 2012 (Nature 487: 477) for the murine colitis model (see Example 1) matches the clinical improvement of human Crohn's disease patients in response to nicotinamide supplementation seen in this example.

Example 3

It turned out surprisingly that although the ACE2 expression in the intestinal mucosa of patients suffering from Crohn's disease and ulcerative colitis did not differ significantly from the values in healthy individuals (data not shown), the expression of $B^0$ AT1 in inflamed portions of the mucosa was reduced very strongly and in a statistically significant way (P value<0.05) (see table 1). In addition, control samples from patients suffering from intestinal inflammations of different genesis (so called disease specificity controls) showed no significant deviation from hospitalized normal persons (FIN). This argues against a general, non-specific deficiency disease or amino acid deficiency and for the specific effects of nicotinic acid, nicotinamide and/or tryptophan (and related compounds) in the treatment of IBD, which effects are newly observed in the present invention.

TABLE 1 mRNA expression of $B^0AT1$ with respect to the base value (from samples of hospitalized normal controls, HN, i.e., patients without intestinal inflammation)

| | Crohn's disease | | Ulcerative colitis | | All inflamed | All non-inflamed | Inflamed samples of other | Non-inflamed samples of other |
|---|---|---|---|---|---|---|---|---|
| | Inflamed | Not inflamed | inflamed | Not inflamed | All IBD samples | IBD samples | IBD samples | intestinal diseases | intestinal diseases |
| Deviation with respect to HN | −8.77 | −1.55 | −31.02 | −2.15 | −5.44 | −18.43 | −1.92 | −1.52 | −1.01 |
| P value | 0.0002 | 0.2772 | 0.0000 | 0.0207 | 0.0000 | 0.0000 | 0.0485 | 0.1093 | 0.3632 |

The tryptophan transporter deficiency observed in IBD patients observed in this example corresponds to the situation in mice with exacerbated colitis due to tryptophan transporter deficiency (Hashimoto et al. 2012, Nature 487: 477; see Example 1).

Example 4

In order to characterise the advantage of controlled release formulations for targeted delivery of nicotinamide to the intestinal epithelium, a proof-of-concept study was conducted in a dextrane sodium sulfate (DSS) colitis model in mice. DSS colitis is a standardised colitis model for drug candidate efficacy evaluation for human inflammatory bowel diseases. As a treatment control normally effective in DSS colitis, 5-aminosalicylic acid (5-ASA) was used. 5-ASA is nearly insoluble at physiological pH and was therefore administered as a suspension in 0.5% methylcellulose.

Due to species-specific differences in the gastrointestinal tract in terms of length, passage time and pH milieu, the controlled release formulations were adapted to the organism which was to be treated. Based on the parameters of the murine gastronintestinal tract (Koopman et al. 1978, Lab. Anim. 12:223; McConnell et al. 2008, J. Pharm. Pharmacol. 60:63), a murine-specific formulation was produced for the proof-of-concept study in mice.

Controlled release minitablets were produced with a powder mixed of 99% NAM and 1% of magnesium stearate (both from Caelo, Hilden, Germany) as lubricant. After blending, the powder was characterised in terms of powder flow (angle of repose; <35°) and size distribution (laser diffraction; main particle fraction: 100-200 µm) to ensure good powder flow. Minitablets were then produced in a rotary press and coated by a film of the water-insoluble polymer Kollidon SR 30 D (BASF, Ludwigshafen, Germany) to control NAM release by diffusion of NAM through the film. The coating formulation was as follows: Kollicoat SR 20 D (49.9%), glycerol monostearate 60 (0.743%), propylene glycol (0.743%), red iron oxide (0.4%), polysorbate 80 (0.314%), and water ad 100%.

The glycerol monostearate 60 (Caelo) was heated with half of the water to 80° C. and emulsified with an Ultraturrax (IKA, Staufen, Germany). Subsequently, the red iron oxide (Caelo) was added and dispersed for additional 5 min (first bin). The polysorbate 80 (Caelo), the propylene glycol (Caelo) and the polymer dispersions were combined in a second bin and stirred with a magnetic stirrer. The cool (<30° C.) emulsion from the first bin was combined with the polymer dispersion from the second bin, and the remaining water was added. The dispersion was stirred for 1 h before filtering (<500 µm). The minitablets were coated in a fluidised bed apparatus (Mycrolab, Hüttlin, Schopfheim, Germany) in a batch size of 50 g with a liquid feed rate of about 1 ml/min and a nebulizing pressure of 0.7 bar. Before spraying, the tablets were pre-heated by a volume flow of 8 $m^3$ at 45° C. During spraying, the volume flow was increased to 16 $m^3$ at 45° C. A product temperature of about 38° C. was observed. After spraying, the tablets were fluidised with 16 $m^3$ for additional 10 min at 45° C. for curing. In the final process step, the heating was switched off and the tablet bed was cooled to <30° C. to avoid sticking. The tablets were coated with 6.2±0.04 mg/cm$^2$. Drug release was determined in a paddle apparatus (DT6, Erweka, Heusenstamm, Germany) in according to the Ph. Eur. at 50 rpm. Phosphate buffer (pH 4) was used as dissolution medium because a slightly acid gastrointestinal fluid of about this pH is expected in mice (McConnell et al. 2008, J. Pharm. Pharmacol. 60: 63-70). The drug concentration was determined by UV absorption at 262 nm. The uncoated tablets showed an instantaneous drug release due to the minuscule size of the tablets and the high water solubility of nicotinamide. Using the Kollidon SR coating, the drug release was optimised to cover the target areas in the small intestine of the mice (at least 15 min lag time, constant drug release over 3 h). The minitablets were homogeneously mixed with the Tryptophan/niacin-free diet powder, pellets of approximately 2 cm length and 1 cm diameter were formed with a minimum amount of sterile water, frozen in single-use aliquots at −20° C. for storage and freshly thawed daily for feeding the mice.

Male C57BL/6J mice (specific pathogen free; Taconic Europe, Ry, Denmark) were taken into the test facility at 6-7 weeks of age and acclimatised for 2 weeks. The diet during the acclimatisation phase was Altromin 1324, produced by Altromin (Lage, Germany). After 2 weeks of acclimatisation, the diet was changed to a custom-made diet without tryptophan or nicotinic acid or nicotinamide (Trp/Nia/NAM-free diet), which was manufactured by Ssniff (Soest, Germany). At the day of the diet change, the treatment regimen started as specified below. Both the Trp/Nia/NAM-free diet and the treatment were administered until termination of the mice. After 12 days of Trp/Nia/NAM-free diet, the mice were challenged with 1.5% DSS (MP Biomedicals, Illkirch, France) in the drinking water for 4 days and then terminated.

The treatment regimen was carried out with four groups of 10 mice each, which were treated as follows:

Group 1: daily oral gavage of 0.25 mL of vehicle (sterile water).

Group 2: daily oral gavage of 0.25 mL of nicotinamide (Cat. No. 4488; Caelo) solution in sterile water (6 mg/mL; final dose: ca. 60 mg/kg bodyweight).

Group 3: Controlled release NAM minitablets homogeneously dispersed in the diet (final dose: ca. 60 mg/kg bodyweight, based on a food intake of 2.5 g per mouse per day).

Group 4: daily oral gavage of 0.25 mL of 5-aminosalicylic acid (5-ASA; Cat. No. A3537, Sigma-Aldrich, Brondby, Denmark) suspended in 0.5% methylcellulose (Cat. No. M7140, Sigma-Aldrich) at a concentration of 15 mg/mL (final dose: ca. 150 mg/kg bodyweight).

Dose solutions were prepared freshly from the same stock solutions every day immediately before administration.

Immediately before changing the diet, before DSS colitis induction and before termination, fresh stool samples equivalent to two fecal pellets were collected from each animal for microbiome analyses. Stool samples were immediately snap-frozen in liquid nitrogen and stored at −80° C. Snap-freezing was performed to maintain the ratios between different bacteria with diverse growth characteristics under ambient conditions.

Immediately after termination of the animals, the colon was washed with 0.9% saline and "Swiss roll" samples were prepared (Moolenbeek and Ruitenberg 1981: Lab. Anim. 15: 57). In brief, the cleaned colon was cut open longitudinally, wrapped up with the villi facing outward, and the resulting roll was fixed in formaldehyde and embedded in paraffin according to standard procedures. The "Swiss roll" preparation enables longitudinal and quantitative histological evaluation of the complete colonic mucosa on the same section slide. Sections were stained with hematoxylin-eosin according to standard procedures. Samples were evaluated by two independent and blinded investigators and scored according to the following system based on three parameters:

Severity of inflammation: 0, rare inflammatory cells in the lamina propria; 1, increased numbers of granulocytes in the lamina propria, submucosal edema; 2, confluence of inflammatory cells extending into the submucosa; 3, transmural extension of the inflammatory infiltrate.

Crypt damage: 0, intact crypts; 1, loss of the basal one-third; 2, loss of the basal two-thirds; 3, entire crypt loss; 4, change of epithelial surface with erosion; 5, confluent erosion.

Ulceration: 0, absence of ulcers; 1, 1 or 2 foci of ulcerations; 2, 3 or 4 foci of ulcerations; 3, confluent or extensive ulceration.

The maximum histological score was 3+5+3=11.

Blinded histological evaluation of the complete colonic mucosa was chosen as a hard endpoint for a therapeutic effect of the claimed NAM formulations.

Figure 3:
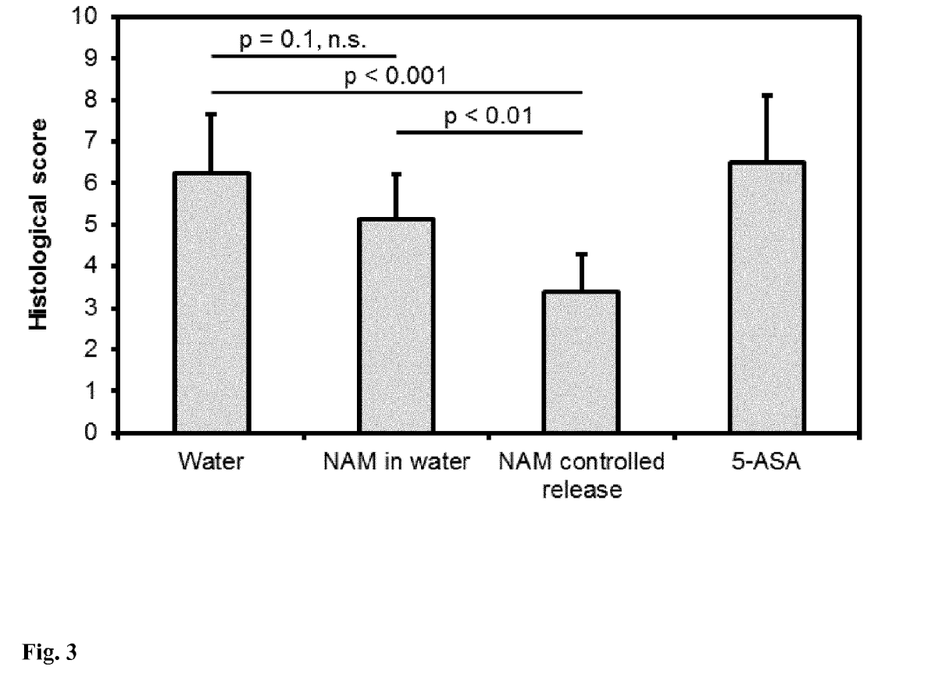
FIG. 3 shows histological scores of the colonic mucosa of mice challenged with dextrane sodium sulfate (DSS) colitis and treated with either nicotinamide (NAM) gavaged in water or a controlled release minitablet formulation of NAM mixed in the diet or 5-aminosalicylic acid gavaged as a suspension in 0.5% methylcellulose.

The histological scores of the four groups are shown in FIG. 3, expressed as means and standard deviations. Only optimally conserved and prepared colon samples and sections were used (number of animals represented in brackets in the following text). The scores were as follows:

group 1 (water control): 6.25±1.39 (n=8);
group 2 (NAM in water): 5.14±1.07 (n=7);
group 3 (NAM controlled release tablets): 3.38±0.92 (n=8);
group 4 (5-ASA): 6.50±1.60 (n=8).

Whereas NAM in the drinking water induced only a tendential decrease in the histological inflammation score compared to the water control ($p=0.1$), a highly significant difference was observed both between NAM controlled release tablets and the water control group ($p<0.001$) and, importantly, also between NAM in water and NAM controlled release ($p<0.01$). Interestingly, the treatment control 5-ASA (which ameliorates normal DSS colitis and is widely used for the therapy of inflammatory bowel diseases in humans) was unable to ameliorate DSS colitis in the absence of tryptophan or niacin (FIG. 3). These findings support the concept of the present invention that the beneficial effects on NAM on the intestinal microbiota and on colitis are not optimally harnessed by systemic delivery via oral gavage, but instead by controlled release formulations in the intestine, and that the primary effect of NAM is on the local environment in the intestine.

Example 5

In order to further characterise the controlled release formulations for targeted delivery of nicotinamide to the intestinal epithelium, a second proof-of-concept study was conducted in a dextrane sodium sulfate (DSS) colitis model in mice. In this second and larger proof-of-concept study, a controlled release granule formulation for NAM was tested in three different doses. As a treatment control normally effective in DSS colitis, controlled release granules containing 5-aminosalicylic acid were used (5-ASA granules; PENTASA, Ferring Pharmaceuticals, Saint-Prex, Switzerland).

The controlled release formulation for NAM is a granulate of 25% nicotinamide, 70% dibasic calcium phosphate and 5% Povidone K30. The mean particle size was 234 µm. The granulate was subsequently film coated with Ethylcellulose 7 to achieve a 30% weight gain and a mean particle size of 640 µm. Filtering removed particles with a size of less than 355 µm. Control granules replaced NAM with an equivalent amount of dibasic calcium phosphate.

Male C57BL/6J mice (specific pathogen free; Charles River Laboratories, Saint-Germain-sur-l'Arbresle, France) were taken into the test facility at >12 weeks of age and acclimatised for 1.5 months in order to enrich and stabilise their microbiota. The diet during the acclimatisation phase was diet A4, produced by SAFE (Scientific Animal Food and Engineering, Augy, France). After the acclimatisation, the diet was changed to a custom-made diet without tryptophan or nicotinic acid or nicotinamide (Trp/Nia/NAM-free diet), which was manufactured by Ssniff (Soest, Germany). The Trp/Nia/NAM-free diet was supplied as a powder, which was used to prepare food pellets with either no granules, control granules without NAM or 5-ASA, NAM granules or 5-ASA granules. Granules were homogeneously dispersed in the diet. Food pellets of approximately 2 cm length and 1 cm diameter were formed with a minimum amount of sterile water, frozen in single-use aliquots at −20° C. for storage and freshly thawed daily for feeding the mice. The granule content of the food pellets was defined as follows with a calculation basis of 30 g bodyweight and a daily food intake of 3 g.

5-ASA granules (target dose of 5-ASA: 150 mg/kg bodyweight; 5-ASA content: 52%): 4.5 mg 5-ASA needed in 3 g of food; 8.65 mg of granules needed in 3 g of food; 2.88 g of granules added per kg of food. The fixed doses for the other granules were calculated in an analogous fashion.

NAM granules (target doses of NAM: 30, 60 or 120 mg/kg bodyweight; NAM content: 19.1%): for 30 mg/kg NAM, 1.57 g of granules per kg of food; for 60 mg/kg NAM, 3.14 g of granules per kg of food; for 120 mg/kg NAM, 6.28 g of granules per kg of food.

Control granules were added to food at the same ratio as the NAM granules of the 120 mg/kg dose group, i.e., 6.28 g of granules per kg of food.

On the day on which the diet was switched to Trp/Nia/NAM-free diet with or without granules, the oral gavage treatment regimen was started for groups 1 and 2 as specified below. Both the Trp/Nia/NAM-free diet with or without granules and the gavage treatment were administered until termination of the mice. After 12 days of Trp/Nia/NAM-free diet, the mice were challenged with 1.5% DSS (TDB Consultancy, Uppsala, Sweden) in the drinking water for five days and terminated after another two days during which they were supplied with normal drinking water.

The treatment regimen was carried out with seven groups of 10 mice each, which were treated as follows:

Group 1: daily oral gavage of 0.1 mL of vehicle (sterile water).
Group 2: daily oral gavage of 0.1 mL of NAM (Sigma-Aldrich, Brondby, Denmark) solution in sterile water (18 mg/mL; final dose: ca. 60 mg/kg bodyweight).
Group 3: control granules in the diet (granule content corresponding to group 6).
Group 4: NAM granules in the diet (final dose: 30 mg/kg bodyweight).
Group 5: NAM granules in the diet (final dose: 60 mg/kg bodyweight).
Group 6: NAM granules in the diet (final dose: 120 mg/kg bodyweight).
Group 7: 5-ASA granules in the diet (final dose: 150 mg/kg bodyweight).

Dose solutions were prepared freshly from the same stock solutions every day immediately before administration.

Immediately before changing the diet, before DSS colitis induction and before termination, fresh stool samples equivalent to two fecal pellets were collected from each animal for microbiome analyses. Stool samples were immediately snap-frozen in liquid nitrogen and stored at −80° C. Snap-freezing was performed to maintain the ratios between different bacteria with diverse growth characteristics under ambient conditions.

Figure 4:
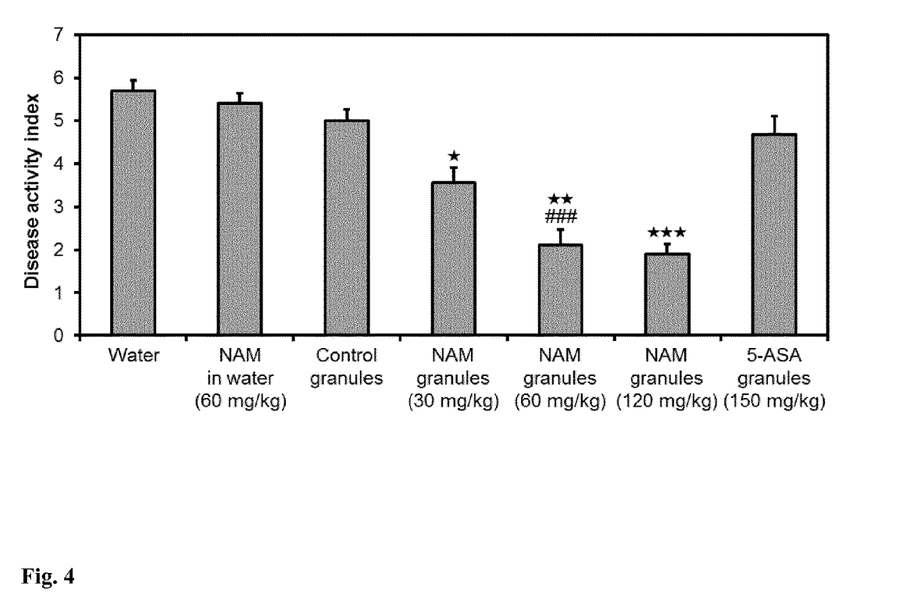
FIG. 4 shows the disease activity index (DAI) data of mice challenged with dextrane sodium sulfate (DSS) colitis and treated with (1) nicotinamide (NAM) gavaged in water, or (2) control granules mixed in the diet, or (3) a controlled release granule formulation of NAM mixed in the diet in three doses, or (4) a controlled release granule formulation of 5-aminosalicylic acid (5-ASA granules) mixed in the diet. *, $p<0.05$ vs. control granules; , $p<0.01$ vs. control granules; *, $p<0.001$ vs. control granules; ###, $p<0.001$ vs. same dose of NAM in water.

From the beginning of the DSS challenge, the mice were monitored daily for their general health condition and the parameters relevant for the disease activity index (DAI), namely diarrhea and visible fecal blood. After termination, a macroscopic scoring of the colonic inflammation was performed. The DAI was calculated according to Melgar et al. 2005 (Am J. Physiol. Gastrointest. Liver Physiol. 288: G1328), which has a theoretical maximum of 9. The DAI data summarised in Table 2 and FIG. 4 show that, similar to the data of Example 4, NAM in water showed only a non-significant trend towards improvement in this experimental setting, whereas the controlled release formulation of NAM (NAM granules) caused a highly significant and dose-dependent reduction of the DAI. Importantly, the NAM granule group receiving 60 mg/kg NAM had a significantly lower DAI than the group receiving 60 mg/kg NAM in water (Table 2). 5-ASA granules showed a non-significant trend towards therapeutic efficacy.

TABLE 2

Disease activity index (DAI) data and their statistical evaluation.

| Group | DAI | Statistical significance |
|---|---|---|
| Water | 5.70 ± 0.24 | not applicable |
| NAM in water (60 mg/kg) | 5.40 ± 0.25 | not significant vs. water |
| Control granules | 5.00 ± 0.25 | not applicable |
| NAM granules (30 mg/kg) | 3.56 ± 0.35 | p = 0.03 vs. control granules |
| NAM granules (60 mg/kg) | 2.11 ± 0.35 | p < 0.01 vs. control granules; p < 0.001 vs. NAM in water (60 mg/kg) |
| NAM granules (120 mg/kg) | 1.90 ± 0.23 | p < 0.001 vs. control granules |
| 5-ASA granules (150 mg/kg) | 4.67 ± 0.42 | not significant vs. water or control granules |

The amount of myeloperoxidase (MPO), an enzyme contained in granules of polymorphonuclear neutrophilic granulocytes, is a quantitative tissue marker for neutrophil recruitment and indirectly allows quantifying the acute colonic inflammation mediated by neutrophils in DSS colitis.

For assaying the MPO content of the murine colonic tissue, representative colon tissue samples were analysed with the Hycult MPO mouse ELISA kit (Cat. No. HK210; Hycult Biotech; CliniSciences, Nanterre, France) according to the manufacturer's recommendations.

Figure 5:
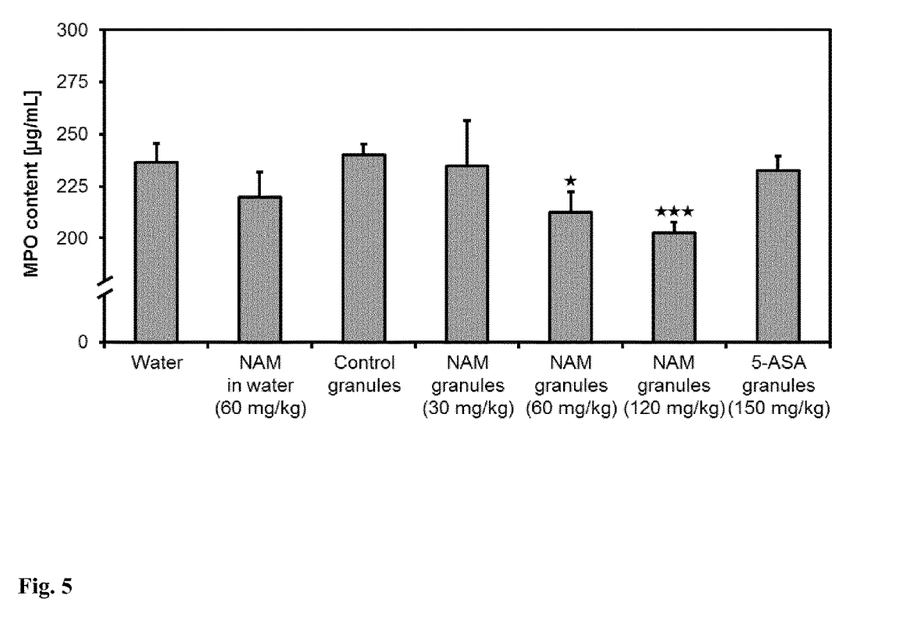
FIG. 5 shows myeloperoxidase (MPO) content of colonic tissue homogenates from mice challenged with dextrane sodium sulfate (DSS) colitis and treated with (1) nicotinamide (NAM) gavaged in water, or (2) control granules mixed in the diet, or (3) a controlled release granule formulation of NAM mixed in the diet in three doses, or (4) a controlled release granule formulation of 5-amino salicylic acid (5-ASA granules) mixed in the diet. *, $p<0.05$ vs. control granules; ***, $p<0.001$ vs. control granules.

Whereas NAM in water showed only a non-significant trend towards MPO reduction, a significant decrease of MPO levels was observed in the groups of mice which received NAM granules at doses of 60 and 120 mg/kg, again indicating a significant therapeutic effect of NAM only when administered as a controlled release formulation (Table 3, FIG. 5).

TABLE 3

Quantification and statistical analysis of myeloperoxidase (MPO) levels in the colon.

| Group | MPO | Statistical significance |
|---|---|---|
| Water | 236.41 ± 9.1 | not applicable |
| NAM in water (60 mg/kg) | 219.71 ± 12.16 | not significant vs. water |
| Control granules | 240.25 ± 5.18 | not applicable |
| NAM granules (30 mg/kg) | 234.61 ± 21.96 | not significant vs. control granules |
| NAM granules (60 mg/kg) | 212.42 ± 10.08 | p < 0.05 (p = 0.036) vs. control granules |
| NAM granules (120 mg/kg) | 202.76 ± 4.97 | p < 0.001 vs. control granules |
| 5-ASA granules (150 mg/kg) | 232.69 ± 6.73 | not significant vs. water or control granules |

Example 6

As the results of both animal studies described in Examples 4 and 5 suggested a significant therapeutic efficacy of NAM controlled-release formulations, the intestinal microbiome of mice from the study described in Example 5 was analysed with exactly the same methodology and machinery (16srDNA phylogenies and 454 tag sequencing) as described by Hashimoto et al. 2012 (Nature 487:477). From the five groups which had received controlled release granules (groups 3-7), eight animals had been selected in a blinded fashion before analysing the disease parameters described in Example 5. Stool samples from all these mice before the nutritional intervention (normal, non-colitogenic flora as a reference point) and after 12 days of Trp/Nia/NAM-free diet (immediately before DSS challenge, see Example 5) were compared.

Figure 6:
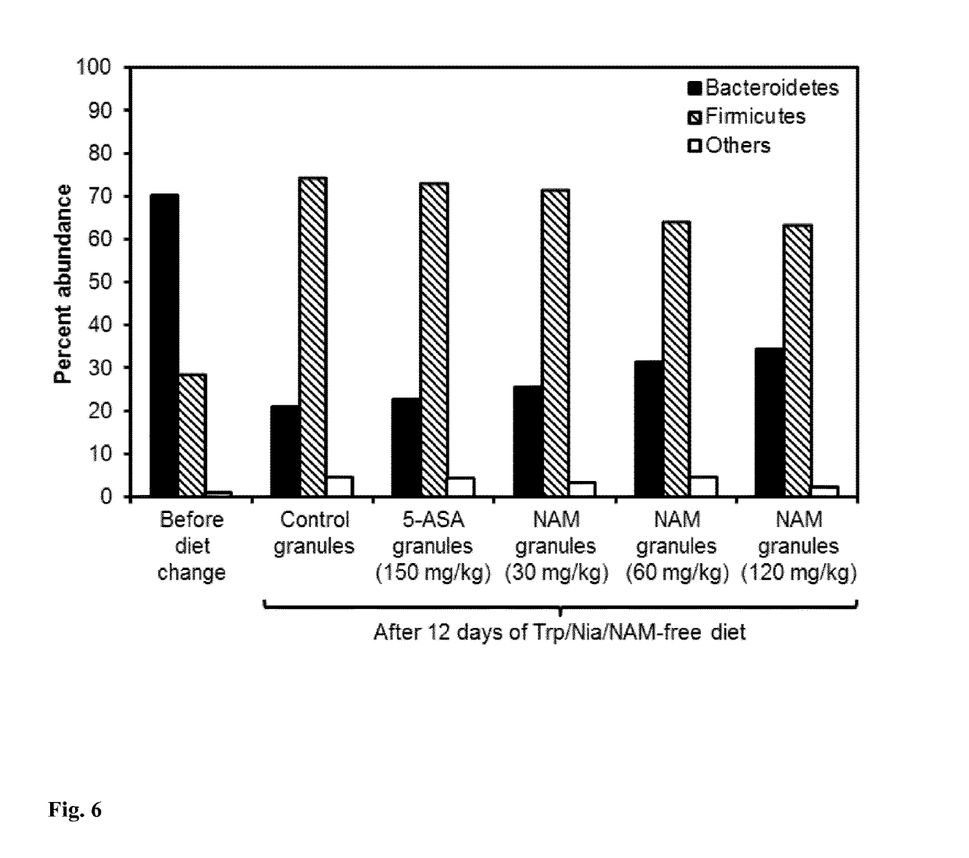
FIG. 6 shows the relative abundance of the main bacterial phyla Bacteroidetes and Firmicutes in stool samples of 5-8 mice per group before and after 12 days of a diet deficient of tryptophan, nicotinic acid or nicotinamide (Trp/Nia/NAM-free diet). The Trp/Nia/NAM-free diet contained (1) control granules without NAM or 5-aminosalicylic acid (5-ASA), (2) a controlled release granule formulation of NAM mixed in the diet in three doses, or (3) a controlled release granule formulation of 5-aminosalicylic acid (5-ASA granules) mixed in the diet.
Figure 7:
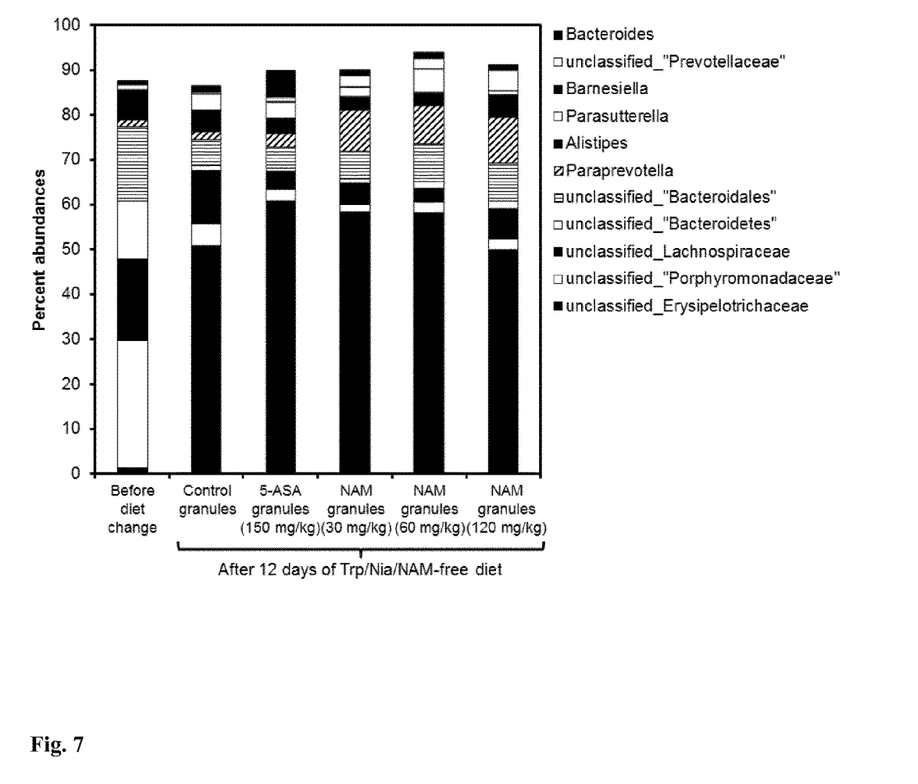
FIG. 7 shows similarity percentage analyses (SIMPER) of the microbiota composition in stool samples of 5-8 mice per group before and after 12 days of a diet deficient of tryptophan, nicotinic acid or nicotinamide (Trp/Nia/NAM-free diet). The Trp/Nia/NAM-free diet contained (1) control granules without NAM or 5-aminosalicylic acid (5-ASA), or (2) a controlled release granule formulation of NAM mixed in the diet in three doses, or (3) a controlled release granule formulation of 5-aminosalicylic acid (5-ASA granules) mixed in the diet. The expansion of unclassified Bacteroidales and the Bacteroidales genus *Paraprevotella* is visualised by the hatched portions of the columns.

FIG. 6 shows that 12 days of Trp/Nia/NAM-free diet led to a dramatic switch of the dominant phylum from Bacteroidetes to Firmicutes. This could partly and dose-dependently be prevented by NAM controlled release granules. 5-ASA controlled release granules showed a trend in the same direction (FIG. 6). In addition, more detailed similarity percentage analyses (SIMPER) of the bacterial groups showed that NAM controlled release induced an expansion of unclassified Bacteroidales and the Bacteroidales genus *Paraprevotella* (FIG. 7; hatched portions of the columns).

Beneficial symbionts of the Bacteroidales order belong to the predominantly represented genera in the mammalian gut and are important for nutrient processing, because they hydrolyse dietary polysaccharides and convert them into short chain fatty acids (SCFAs) which can be utilised by the host. The most homologous genomes to the ones found in the Bacteroidales group expanding under treatment with NAM controlled release granules belonged to such SCFA producers. Of particular relevance, the prevalence of these beneficial symbionts and the resulting levels of intestinal SCFAs are reduced in human inflammatory bowel diseases (Frank et al. 2007, Proc. Natl. Acad. Sci. USA 104: 13780). Expansion of such microbiota by pre- or probiotics as well as their SCFA products have been shown to be therapeutically effective in rodent DSS colitis (Osman et al. 2006, BMC Gastroenterol. 28; 6:31; Maslowski et al. 2009, Nature 461:1282). In addition, Bacteroidales have been shown to secrete immunomodulatory carbohydrate structures (polysaccharide A) which may suppress inflammatory responses (Mazmanian et al. 2008, Nature 453:620).

In summary, controlled release of NAM in the intestine leads to a dose-dependent increase in beneficial microbiota and reduces colitis.

The examples above serve to explain the invention, but are not intended to limit the scope.

The invention claimed is:

1. An oral pharmaceutical composition for positively influencing intestinal microbiota, comprising an active substance selected from the group consisting of nicotinic acid; nicotinamide; tryptophan; nicotinic acid esters; nicotinamide adenine dinucleotide (NAD); nicotinamide adenine dinucleotide phosphate (NADP); an intermediate in the biosynthesis of NAD or NADP selected from N-formylkynurenine, L-kynurenine, 3-hydroxy-L-kynurenine, 3-hydroxyanthranilate, 2-amino-3-carboxymuconate semialdehyde, quinolinate, and beta-nicotinate D-ribonucleotide; a tryptophan dipeptide; or a combination of two or more thereof, formulated for selective release in the terminal ileum, the colon, or both, for topical efficacy in the terminal ileum, the colon, or both, where the intestinal microbiota to be influenced are located,
  wherein the oral pharmaceutical composition is formulated for oral administration and comprises (a) a matrix that comprises the active substance(s), wherein the matrix comprises one or more selected from microcrystalline cellulose, gelatin, and polyvinylpyrrolidone, and, optionally, (b) a coating, wherein the oral pharmaceutical composition selectively releases the active substance(s) in the terminal ileum, the colon, or both for topical efficacy in the terminal ileum, the colon, or both, to thereby positively influence intestinal microbiota.

2. The pharmaceutical composition according to claim 1, wherein the composition comprises an active substance selected from the group consisting of nicotinic acid, nicotinamide, tryptophan, tryptophan dipeptide, and combinations of two or more thereof.

3. The pharmaceutical composition according to claim 1, wherein the composition comprises nicotinamide as an active substance.

4. The pharmaceutical composition according to claim 1, wherein the composition comprises (i) nicotinic acid and/or nicotinamide and (ii) acetylsalicylic acid as active substances.

5. The pharmaceutical composition according to claim 1, wherein the composition comprises tryptophan dipeptide as an active substance.

6. The pharmaceutical composition according to claim 1, wherein the oral composition is formulated for oral administration to provide delayed release of the active substance(s) for specific local effect in the terminal ileum and/or colon.

7. The pharmaceutical composition according to claim 1, wherein the oral composition is formulated for oral administration to provide controlled release of the active substance(s) for specific local effect in the terminal ileum and/or colon.

8. The pharmaceutical composition according to claim 1, formulated as an oral dosage form with an active substance content of 1-3000 mg per finished dosage form.

9. The pharmaceutical composition according to claim 1, formulated as an oral dosage form with an active substance content of 100-1000 mg per finished dosage form.

10. A therapeutic method comprising orally administering a composition according to claim 1 to a subject in need thereof.

11. The method of claim 10, wherein the method is for the therapy of one or more conditions selected from the group consisting of inflammatory bowel disease, colon carcinoma, and diseases of other body organs which result from changes in the intestinal microbiota and/or an impaired interaction between intestinal microbiota and intestines.

12. The method of claim 10, wherein the method is for the therapy or prophylaxis of inflammatory bowel disease.

13. The method of claim 12, wherein the inflammatory bowel disease is ulcerative colitis or Crohn's disease.

14. The method of claim 10, wherein the method is for positively influencing the intestinal microbiota.

15. The method of claim 10, wherein the composition is formulated for oral administration to provide delayed release of the active substance(s) for specific local effect in the terminal ileum and/or colon, wherein the method provides delayed release of the active substance(s).

16. The method of claim 10, wherein the method is for the therapy of one or more conditions selected from the group consisting of inflammatory diseases of the small intestine, diseases of the large intestine, colon carcinoma, and diseases that result from changes in the intestinal microbiota and/or impaired interaction between intestinal microbiota and intestines.

17. The method of claim 10, wherein the composition is formulated for oral administration to provide controlled release of the active substance(s) for specific local effect in the terminal ileum and/or colon, wherein the method provides controlled release of the active substance(s).

18. The method of claim 10, wherein the composition further comprises a prostaglandin D2 antagonist.

19. The pharmaceutical composition according to claim 1, wherein the matrix selectively releases the active substance(s) in the terminal ileum, the colon, or both, for topical efficacy in the terminal ileum, the colon, or both.

20. The pharmaceutical composition according to claim 1, wherein the oral composition further comprises the coating.

21. The pharmaceutical composition according to claim 19, wherein the matrix is based on a multi matrix (MMX) technology and selectively releases the active substance(s) in the terminal ileum, the colon, or both, for topical efficacy in the terminal ileum, the colon, or both.

22. The pharmaceutical composition according to claim 1, wherein the oral composition is formulated with the coating, wherein the coating selectively releases the active substance(s) in the terminal ileum, the colon, or both, for topical efficacy in the terminal ileum, the colon, or both.

23. The pharmaceutical composition according to claim 22, wherein the coating releases the active substance(s) at pH>6.4.

24. The pharmaceutical composition according to claim 1, further comprising a prostaglandin D2 antagonist.

* * * * *

UNITED STATES PATENT AND TRADEMARK OFFICE
CERTIFICATE OF CORRECTION

PATENT NO.        : 10,426,765 B2
APPLICATION NO.   : 14/407780
DATED             : October 1, 2019
INVENTOR(S)       : Georg Waetzig and Dirk Seegert It is certified that error appears in the above-identified patent and that said Letters Patent is hereby corrected as shown below:

On the Title Page

Item (57) (Abstract)
Line 2, commencing on Line 3, please replace "tryptophanor" with --tryptophan or--

Signed and Sealed this
Seventh Day of April, 2020

Andrei Iancu
*Director of the United States Patent and Trademark Office*